United States Patent [19]

Kido et al.

[11] Patent Number: 4,526,866
[45] Date of Patent: Jul. 2, 1985

[54] ANGIOTENSIN I-CONVERTING ENZYME INHIBITOR AND PREPARATION OF THE SAME

[75] Inventors: Yasuji Kido; Tsutomu Yoshida; Toshinari Hamakado; Masami Anno; Takahiro Harada; Yoshinobu Motoki, all of Yamaguchi, Japan

[73] Assignee: Fujizoki Pharmaceutical Co., Ltd., Tokyo, Japan

[21] Appl. No.: 482,356

[22] Filed: Apr. 5, 1983

[30] Foreign Application Priority Data

Apr. 13, 1982 [JP] Japan .................................. 57-60381

[51] Int. Cl.³ ........................ C12P 21/00; C12P 1/06; C12R 1/465

[52] U.S. Cl. ...................................... 435/68; 435/169; 435/886; 260/112 R

[58] Field of Search .............. 435/68, 169; 260/112 R

[56] References Cited

U.S. PATENT DOCUMENTS 4,404,282  9/1983  Nakatsukasa ........................ 435/122

Primary Examiner—Lionel M. Shapiro
Attorney, Agent, or Firm—Flynn, Thiel, Boutell & Tanis

[57] ABSTRACT

A novel enzyme inhibitor of angiotensin I-converting enzyme was produced from an actinomycetes belonging to genus Streptomyces. This enzyme inhibitor is a peptide, and specifically inhibits the angiotensin I-converting enzyme, but does not inhibit thermolycin, pepsin and α-chymotrypsin.

4 Claims, 3 Drawing Figures

ANGIOTENSIN I-CONVERTING ENZYME INHIBITOR AND PREPARATION OF THE SAME

BACKGROUND OF THE INVENTION

1. Field of the Invention

This invention relates to an angiotensin I-converting enzyme inhibitor IS83 (hereinafter referred to as ACE inhibitor IS83 or IS83 in short), and its preparation method.

2. Description of the Prior Art

Angiotensin I is converted to angiotensin II by the action of an angiotensin I-converting enzyme. Angiotensin II has an activity to raise blood pressure. Accordingly, an ACE inhibitor can be used as a depressor.

Various angiotensin I-converting enzyme inhibitors have been reported. They are obtained from a snake poison or synthesized.

SUMMARY OF THE INVENTION

We found that a novel ACE inhibitor IS83 is produced by a microorganism belonging to the genus Streptomyces. The present invention is based on this discovery.

DETAILED DESCRIPTION OF PREFERRED EMBODIMENTS

Figure 1:
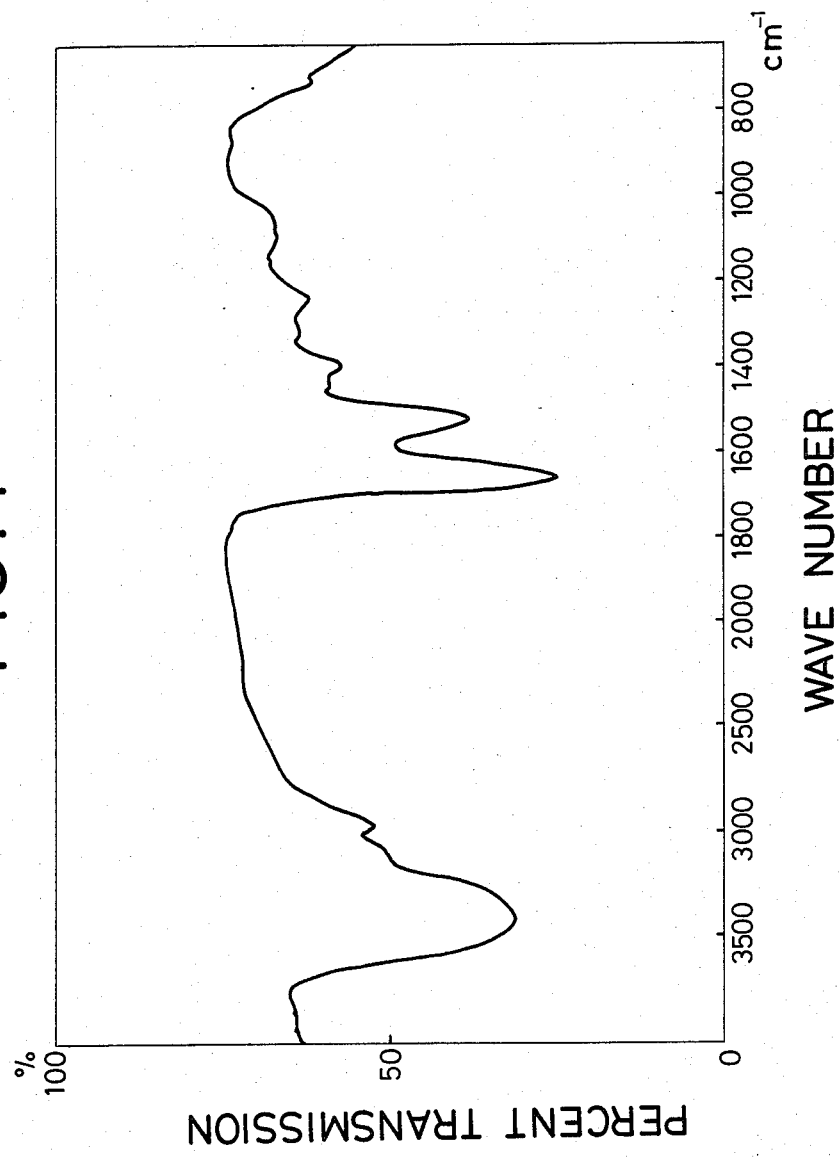
FIG. 1 shows an infrared absorption spectrum of IS83 pelleted with potassium bromide.

A microorganism used in this invention is Streptomyces sp No. 1647P-2 strain, which has been obtained from soils in Saitama prefecture, Japan. This strain has been named Streptomyces sp No. 1647-P2 and deposited at the Fermentation Research Institute, the Agency of Industrial Science and Technology, Japan, under the deposition number FERM-P No. 6343.

This strain has microbiological characteristics as shown below:

1. Morphological properties:

Substrate mycelium is well branched, and fragmentation of substrate mycelium usually does not occur. Aerial mycelium elongates from substrate mycelium, and is simple branching from main stem to form sporophore. Its top is open loop or irregularly spiral. The number of spores in the chain is 3 to 10, and the surface of the spore is smooth. Size of the spore is $0.5-0.8 \times 1.0-1.5\mu$, oblong or oval. Flagellospore, sporangium, sclerotium and whorl verticillate are not recognized.

2. Growth on media:

(1) Sucrose-nitrate agar medium
  Growth (G): Poor, Colorless
  Aerial mycelium (AM): Poor, White
  Reverse side (R): Colorless
  Soluble pigment (SP): None (2) Glucose-asparagine agar medium
  G: Good, Yellowish orange
  AM: Moderate, Light yellow
  R: Yellowish orange
  SP: None (3) Glycerin-asparagine agar medium
  G: Good, Yellow
  AM: Moderate, Light yellow
  R: Yellow
  SP: None (4) Starch-inorganic salt agar medium
  G: Good, yellowish orange
  AM: Moderate, Light yellow
  R: Yellowish orange
  SP: None (5) Tyrosine agar medium
  G: Moderate, Yellowish brown
  AM: Not produced
  R: Yellowish brown
  SP: None (6) Nutrient agar medium
  G: Moderate, Light yellowish brown
  AM: Not produced
  R: Light yellowish brown
  SP: None (7) Oatmeal agar medium
  G: Good, Yellow
  AM: Poor, White
  R: Yellow
  SP: None (8) Yeast extract-malt extract agar medium
  G: Good, Light yellow
  AM: Not produced
  R: Light yellow
  SP: None
  Incubation at 28° C.

3. Physiological properties (1) Temperature range for growth: 14.5°–38.0° C.
  Optimum temperature: 27°–31° C.
(2) Liquefaction of gelatin (Glucose-peptone gelatin medium): Negative
(3) Hydrolysis of starch (Starch agar medium): Positive
(4) Coagulation of skim milk: Negative
(5) Peptonization of skim milk: Positive
(6) Reduction of nitrate: Positive
(7) Production of melanine-like pigment is not observed on tyrosine agar medium and peptone-yeast extract-iron agar medium.

4. Utilization of carbon sources (Pridham-Gottlieb agar medium)

D-glucose, L-arabinose, D-xylose, sucrose and inositol are utilized well, but D-fructose, L-rhamnose, D-manitol and raffinose are not utilized.

5. Constituents of Cell Wall

Diaminopimelic acid contained in cell wall is LL-type.

Among the above properties, from the formation of aerial mycelium, the formation of spores on aerial mycelium and the spores in chain, the strain No. 1647P-2 clearly belongs to genus Streptomyces. However, as the ability of this strain to form aerial mycelium is extremely weak, it is difficult to determine the species of this strain. Accordingly, this strain is called Streptomyces sp. No. 1647P-2.

The microorganism employable to the present invention is not limited to the strain No. 1647P-2, and include various variants and mutants of this strain which are able to produce ACE inhibitor IS83. These variants and mutants may be produced by means of the known variation or mutation method, such as ultraviolet irradiation, radiation, irradiation of high frequencies, and the treatment with various chemical reagents. The variation and mutation also occur naturally.

Usual liquid media containing carbon and nitrogen sources, inorganic salts and a small amount of nutrients can be used as a culture medium for IS83-producing microorganism.

Carbohydrates such as glucose, maltose, sucrose and soluble starch are used for a carbon source. Ammonium salts such as ammonium sulfate, ammonium chloride, ammonium phosphate, nitrates such as sodium nitrate, amino acids, and peptone and soy bean powder (or hydrolyzate thereof) are used for a nitrogen source. Inorganic salts such as phosphates are added to the culture media. Further, amino acids, vitamines, peptone and yeast extract may be used for organic nutrient source.

The cultivation is usually carried out at pH 5 to 10 at 15° to 35° C. under aerobic conditions.

ACE inhibitor IS83 of this invention is produced extracellularly, and it can be recovered by means of butanol extraction, dialysis, ion-exchange, adsorption and chromatography such as gel filtration.

For example, mycelia are removed from the culture broth, and the culture filtrate is passed through the column of Diaion HP-30 (manufactured by Mitsubishi Chemical Industries Ltd., Japan). The column is washed with water, and eluted with methanol acidified with HCl. Active fraction is concentrated under reduced pressure, and poured to weakly acidic ion-exchange resin such as CM-Sephadex C-25 (manufactured by Pharmacia AB, Sweden) equilibrated with 0.005M acetic acid buffer solution and then eluted with 0.005M acetic acid buffer solution. The eluate containing ACE inhibitor IS83 is poured to Diaion HP-30 and washed with water, and then eluted with methanol. The eluate is evaporated and dried to solid to obtain crude ACE inhibitor IS83. Crude IS83 can be purified by repeating chromatography with CM-Sephadex C-25. Pure IS83 can be obtained by the steps of: treating by liquid chromatography, in which Radialpack A (particle size: 5 $\mu$m, 0.8 (i.d.)$\times$10 cm, sold by Waters Co.) is used as a column and acetonitrile-0.05M $(NH_4)_2HPO_4$ (22:78) is used as an eluent, treating the eluate with Diaion HP-30 column chromatography to adsorb IS83 on it, washing it with 0.1N HCl and then with water, eluting it with methanol, condensing the eluate, and freeze-drying the condensate to obtain white powders.

ACE inhibitor IS83 of this invention is a peptide and has the characteristics as shown below:

(a) IS83 has inhibitory activity on angiotensin I-converting enzyme, but no inhibitory activity on thermolycin, pepsin and $\alpha$-chymotrypsin as follows:

Angiotensin I-converting enzyme: 100%
Thermolycin: 0%
Pepsin: 0%
$\alpha$-chymotrypsin: 0%

These values have been obtained by using an aqueous solution of IS83 of 7.6 $\mu$g/ml.

Figure 3:
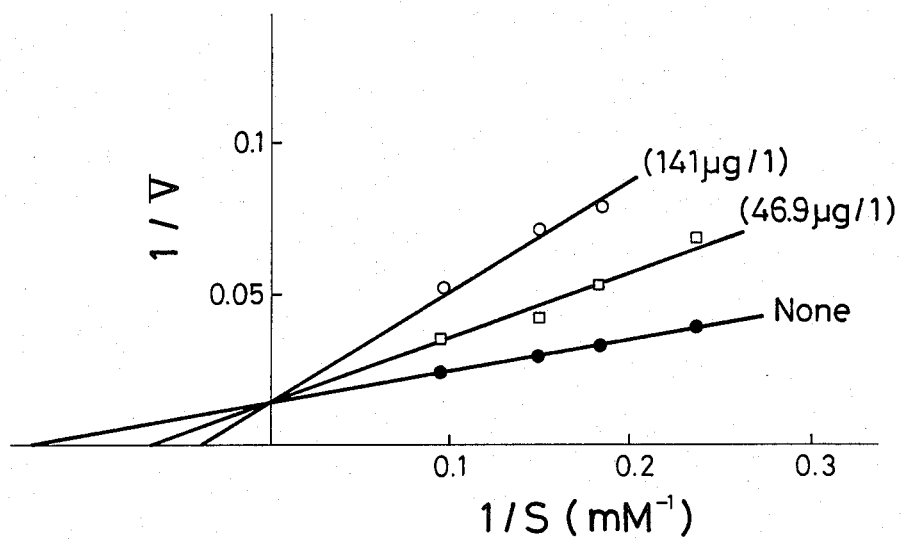
FIG. 3 shows Lineweaver-Burk plot of IS83 in order to determine its inhibition type.

When p-nitrobenzoylglycylglycylglycine is used as substrate, Lineweaver-Burk plot in FIG. 3. In this figure, the number of abscissa indicate the reciprocal of the concentration of the substrate, and the number of ordinate indicate the reciprocal of the reaction rate. Open circles indicate in the case of 141 $\mu$g/l of IS83, squares indicate in the case of 46.9 $\mu$g/l of IS83, and closed circles indicate that IS83 is absent.

As can be seen from the figure, the type of inhibition of IS83 is competitive inhibition.

(b) Specific rotation: $[\alpha]_D = -45.2°$ (C=0.5%, $H_2O$)
(c) Stable pH range: Stable in an acidic condition
(d) Molecular weight: 1962 (from fast atom bombardment mass spectrum)

(e) Infrared absorption spectrum: IR-spectrum with KBr tablet is shown in FIG. 1.

Figure 2:
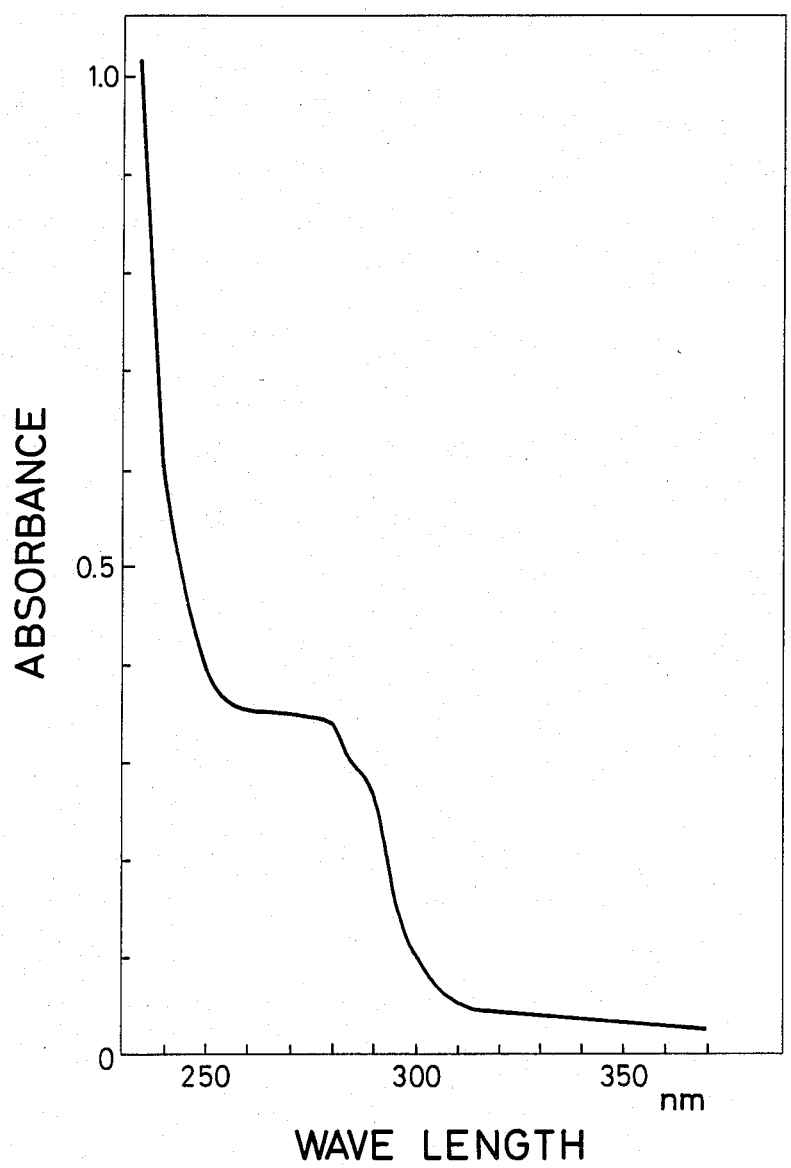
FIG. 2 shows an ultraviolet absorption spectrum of IS83 in its aqueous solution.

(f) Ultraviolet absorption spectrum: UV-spectrum is shown in FIG. 2, which is measured by using aqueous solution of 1.122 mg of IS83 in 10 ml of water.

(g) Solubility in solvents:
Soluble in water and methanol.
Insoluble in ether and acetone.

(h) Color reaction:
Ninhydrin reaction: positive
Triphenyltetrazolium chloride reaction: negative
$\alpha$-naphthol-sulfuric acid reaction: negative (i) Appearance: White powders (j) Melting point: 240°–260° C. (slowly change from white to black)

(k) Rf values obtained by thin layer chromatography:

| Solvent system | Rf Value |
|---|---|
| (1) Cellulose plate (manufactured by Merck Co.) | |
| n-butanol-methanol-water (20:5:10) | 0.73 |
| n-butanol-pyridine-acetic acid-water | |
| (15:10:3:12) | 0.70 |
| (2) Kiesel gel 60 $F_{254}$ plate (manufactured by Merck Co.) | |
| n-butanol-methanol-water (20:5:10) | 0.31 |

(l) Amino acids constituting IS83: IS83 is composed of the following 17 amino acid residues: Tryptophan (1), lysine (1), aspartic acid (2), serine (1), glutamic acid (1), threo-$\beta$-methyllanthionine (3), meso-lanthionine (1), proline (1), glycine (2), valine (1), leucine (1), phenylalanine (1) and dehydroalanine (1).

Assay of enzyme inhibitory activity:
(i) Sample is dissolved in 0.1M tris-HCl buffer solution (pH 8.0) containing 0.3M sodium chloride. 0.125 ml of this sample solution is mixed with 0.2 ml of 16.0 mM p-nitrobenzoylglycylglycylglycine which is dissolved in 0.3M tris-HCl buffer solution (pH 8.0) containing 0.3M sodium chloride, and allowed to stand at 37° C. for 5 minutes. 0.1 ml of the solution of angiotensin I-converting enzyme which is dissolved in 0.1M tris-HCl buffer solution (pH 8.0) containing 0.3M sodium chloride is added to the mixed solution, and reacted at 37° C. The reaction is stopped by the addition of 0.2 ml of aqueous ammonia.

The prescribed amount of the reactant is injected into a column of high performance chromatography, and the amount ($I_s$) of p-nitrobenzoylglycine is determined by using the calibration curve which is obtained by using pure p-nitrobenzoylglycine as a standard.

(ii) Except that 0.1M tris-HCl buffer solution (pH 8.0) containing 0.3M sodium chloride is employed instead of the above sample solution, the amount ($I_c$) of p-nitrobenzoylglycine is determined according to the same manner as above.

(iii) Except that angiotensin I-converting enzyme is added to the above reactant instead of the above mixed solution, the amount ($I_b$) of p-nitrobenzoylglycine is determined according to the same manner as described in item (a).

Inhibition percent is calculated as follows:

$$\frac{I_c - I_s}{I_c - I_b} \times 100\%$$

The present invention is further illustrated by the following example.

EXAMPLE

A culture medium for seed culture containing 1% glucose, 1% glycerol, 1% soy bean flour, 0.5% ammonium sulfate, 0.4% sodium chloride, 0.4% calcium carbonate, 0.25% yeast extract, 0.2% meat extract, 0.05% $K_2HPO_4$, and 0.05% $MgSO_4$ of pH 7.2 was prepared. Each 50 ml of this culture medium was placed in twelve 500 ml Erlenmeyer flasks, and sterilized at 120° C. for 20 minutes. Each one loopful of Streptomyces sp. No. 1647-P2 collected from its slant culture was inoculated to each sterilized culture medium, and cultured at 28° C. for 4 days with shaking at 210 rpm.

30 l of a culture medium containing 3% glycerol, 1.5% casein, 0.4% soy bean flour, 0.5% ammonium sulfate, 0.4% calcium carbonate, 0.4% sodium chloride, 0.25% yeast extract, 0.1% meat extract, 0.05% $K_2HPO_4$, and 0.05% $MgSO_4$ was placed in a 50 l jar fermenter, and sterilized. This sterilized culture medium was inoculated with 600 ml of the above seed culture, and cultured at 28° C. During the culturing, the culture medium was aerated with 30 l of germfree air per minute, and stirred at 300 rpm. After 65 hours, the cultivation was stopped, and microbial cells were removed by centrifuging. 22 Liters of the supernatant was thus obtained. The inhibition percent of 21 $\mu l$ of the diluted supernatant which was diluted 200 times against angiotensin I-converting enzyme was measured, and found to be 50%.

This supernatant was passed through the column packed with 2.4 l of Diaion HP-30. Then, the column was washed with water, and IS83 was eluted with methanol acidified with HCl. About 2 l of the eluate containing IS83 was concentrated under reduced pressure, and the concentrate was passed through the column packed with 120 ml of CM-Sephadex C-25 of $H^+$ type. The column was washed with water, and IS83 was eluted with 0.2M aqueous sodium chloride solution. The eluate containing IS83 was desalted by using 1.2 l of Diaion HP-30 and according to the previously described method, and concentrated under reduced pressure. The concentrate containing IS83 was poured to the column of CM-Sephadex C-25 (190 ml) previously equilibrated with pH 5.0 of 0.005M acetate buffer solution, and developed with water. The fractions containing active substance were collected, and concentrated under reduced pressure. This purification procedure using CM-Sephadex C-25 column was further repeated twice, and 0.69 g of crude IS83 was obtained.

The crude IS83 was fractionated by high performance liquid chromatography using a column of Radialpack A (particle size: 5 $\mu m$, 0.8 (i.d.)×10 cm, sold by Waters Co.). As the eluent, acetonitrile-0.05M $(NH_4)_2HPO_4$ (22:78) was employed, and the fractions containing IS83 were collected. IS83 in the fractions was adsorbed on the column of Diaion HP-30, and the column was washed with 0.1N HCl and then with water. The adsorbed IS83 was eluted with methanol, and concentrated under reduced pressure. The concentrate was lyophilized to obtain white powder of highly pure IS83. The yield was 70%.

We claim:

1. An angiotensin I-converting enzyme inhibitor IS83 being a polypeptide and having the following properties:
    (a) having an inhibitory activity on angiotensin I-converting enzyme, but substantially no inhibitory activity on thermolycin, pepsin and α-chymotrypsin,
    (b) having a molecular weight of 1962 determined from fast atom bombardment spectrum,
    (c) having a melting point in the range of 240° to 260° C. (decomposition),
    (d) being composed of 17 structural units of amino acid residues which are one residue of tryptophan, one residue of lysine, two residues of aspartic acid, one residue of serine, one residue of glutamic acid, three residues of threo-β-methyllanthionine, one residue of meso-lanthionine, one residue of proline, two residues of glycine, one residue of valine, one residue of luecine, one residue of phenylalanine and one residue of dehydroalanine as its constituents, and
    (e) having an infrared absorption spectrum with potassium bromide tablet as shown in FIG. 1 of the attached drawings and an aqueous solution of 1.122 mg of said enzyme inhibitor IS83 in 10 ml of water having an ultraviolet absorption spectrum as shown in FIG. 2 of the attached drawings.

2. A process for producing angiotensin I-converting enzyme inhibitor IS83 as claimed in claim 1, which comprises, culturing a strain of Streptomyces sp. No. 1647P-2 (FERM P-No. 6343) and mutations thereof, capable of producing said enzyme inhibitor IS83, in an aqueous culture medium containing assimilable sources of carbon and nitrogen, inorganic salts and organic nutrients, and recovering the accumulated enzyme inhibitor IS83 from the culture broth.

3. An angiotensin I-converting enzyme inhibitor IS83 as claimed in claim 1 which has a specific rotation $[\alpha]_D = -45.2°$ (C=0.5%, $H_2O$), which is soluble in water and methanol and is insoluble in ether and acetone, which exhibits the following color reactions
    ninhydrin reaction: positive
    triphenyltetrazolium chloride reaction: negative
    α-naphthol-sulfuric acid reaction: negative
and which exhibits the following Rf values obtained by thin layer chromatography:

| Solvent system | Rf Value |
| --- | --- |
| (1) Cellulose plate (manufactured by Merck Co.) | |
| n-butanol-methanol-water (20:5:10) | 0.73 |
| n-butanol-pyridine-acetic acid-water (15:10:3:12) | 0.70 |
| (2) Kiesel gel 60 $F_{254}$ plate (manufactured by Merck Co.) | |
| n-butanol-methanol-water (20:5:10) | 0.31 |

4. An angiotensin I-converting enzyme inhibitor IS83 which has been prepared by the process of claim 2.

* * * * *